(12) United States Patent  
Davey

(10) Patent No.: US 6,715,365 B2  
(45) Date of Patent: Apr. 6, 2004

(54) SYSTEM AND METHOD FOR THE DETECTION AND PROPAGATION MEASUREMENT OF FLAWS IN A COMPONENT OR STRUCTURE

(75) Inventor: Kenneth John Davey, Perth (AU)

(73) Assignee: Structural Monitoring Systems, Ltd., West Perth (AU)

( * ) Notice: Subject to any disclaimer, the term of this patent is extended or adjusted under 35 U.S.C. 154(b) by 231 days.

(21) Appl. No.: 09/848,648

(22) Filed: May 3, 2001

(65) Prior Publication Data

US 2002/0002866 A1 Jan. 10, 2002

(30) Foreign Application Priority Data

May 3, 2000 (AU) .................................................. 7266

(51) Int. Cl.[7] .............................................. G01N 19/08
(52) U.S. Cl. ....................................................... 73/799
(58) Field of Search ........................ 73/37, 37.5, 37.7, 73/37.9, 38, 40, 820, 799

(56) References Cited

U.S. PATENT DOCUMENTS

| | | |
|---|---|---|
| 3,918,291 A | 11/1975 | Pauly et al. |
| 4,104,906 A | 8/1978 | Oertle |
| 4,145,915 A | 3/1979 | Oertle et al. |
| 4,651,557 A | 3/1987 | Cholet |
| 4,776,206 A | 10/1988 | Armstrong et al. |
| 4,979,390 A | 12/1990 | Schupack et al. |
| 5,078,005 A | 1/1992 | Krempel et al. |
| 5,205,173 A | 4/1993 | Allen |
| 5,404,747 A | 4/1995 | Johnston et al. |
| 5,544,520 A | 8/1996 | Graf et al. |
| 5,596,137 A | 1/1997 | Perry et al. |
| 5,770,794 A | 6/1998 | Davey |
| 6,223,587 B1 | 5/2001 | Chiocca |
| 6,539,776 B2 * | 4/2003 | Davey ........................... 73/37 |

FOREIGN PATENT DOCUMENTS

| | | |
|---|---|---|
| EP | 0 177 433 | 8/1985 |
| SU | 1710929 A | 2/1992 |
| WO | WO 94/27130 | 11/1994 |

\* cited by examiner

*Primary Examiner*—M. Noori
(74) *Attorney, Agent, or Firm*—Allen, Dyer, Doppelt, Milbrath & Gilchrist, P.A.

(57) ABSTRACT

A system 10 for continuously monitoring the integrity of a structure 14 includes a sensor pad 16 having a surface 18. The surface 18 is provided with a set of first channels 22 and interspersed second channels 24. Surface 18 is sealed onto the surface 12 of structure 14 so that the channels 22, 24 together with surface 12 form respective sets of first and second cavities 26 and 28. The first cavities 26 are placed in fluid communication with a vacuum source 101 via a third channel 30. The second cavities 28 are vented to the atmosphere via a fourth channel 34, through hole 35, and conduit 36. A high impedance 102 is placed in series between the vacuum source 101 and the first cavities 26. A differential pressure transducer 103 is connected across the high impedance 102 and monitors for change in vacuum condition between the vacuum source 101 and the vacuum in the cavities 26. If a fault 40 were to develop in structure 14 opening onto surface 12 and propagate to form a fluid communication path between one of the cavities 26 and adjacent cavity 28 there will be a change in the vacuum condition of the cavity 26 which will be detected by the transducer 103.

30 Claims, 8 Drawing Sheets

SYSTEM AND METHOD FOR THE DETECTION AND PROPAGATION MEASUREMENT OF FLAWS IN A COMPONENT OR STRUCTURE

FIELD OF THE INVENTION

The present invention relates to a system and method for use in the continuous monitoring of the structural integrity of a component or structure and in particular for monitoring the integrity of a structure or component to provide an early indication and location of an impending flaw such as a fault or crack and to monitor the growth of the fault or crack.

BACKGROUND OF THE INVENTION

A very important function of design and maintenance engineers is to monitor for, locate and assess the initial location of surface faults or cracks that develop in structures or components under static or dynamic loads and subsequently determine the likely propagation path and rate of growth of the fault or crack. Examples where the monitoring of surface faults and cracks may be critical include on wing sections of aircraft; turbine blades on jet engines, the hull of a ship and the boiler of a nuclear power plant. Often, the monitoring is by visual inspection only. However it will be appreciated that when faults or cracks initially develop they are often extremely small and imperceptible to the eye. Alternately, the faults or cracks may arise in structures or components that are physically difficult or indeed impossible to access.

A system to measure microscopic crack growth rate must have high sensitivity. International Application No PCT/AU94/00325 (WO 94/27130) in the name of Tulip Bay discloses a monitoring apparatus that can be used to detect faults or cracks in the surface of a structure. The monitoring apparatus described includes a substantially constant vacuum source connected in series with a high impedance to fluid flow device that in turn is connected with one or more minuscule flaw sensing cavities formed on the surface of a structure. A differential pressure transducer is connected across the high impedance to fluid flow device to monitor the vacuum state of the minuscule flaw sensing cavity or cavities relative to the constant vacuum source. Accordingly, if there is a change in vacuum condition in the cavities which can arise from the formation and propagation of a crack, the change is detected by the transducer. With this method, cracks of a length down to 250 micron have been detected using a constant vacuum source of only 20 kPa below atmospheric reference. Upon initial indication, minuscule increase in crack growth can be detected. Embodiments of the present device and method are suited for use with the monitoring apparatus described in the aforementioned International application.

Oertle in (U.S. Pat. No. 4,145,915) and (U.S. Pat. No. 4,109,906) claims early crack detection but lacks the sensitivity and practicality to carry out the proposed tasks. This arises because in Oertle, the whole vacuum system volume forms part of a flaw sensing cavity and therefore relatively high vacuum must be employed in order to provide some sensitivity to the method. This becomes obvious if a constant vacuum source of only 20 kPa below atmospheric reference were to be used by Oertle. Further, the use of high vacuum dictates the use of low permeability materials which limits practical application.

Tulip Bay (WO 94/27130) has the advantage that the flaw sensing cavity is, to a large extent, isolated from the vacuum source and can therefore be of minuscule volumetric capacity.

SUMMARY OF THE INVENTION

Objects of the present invention include: to provide a system and method for continuous monitoring of a structure or component to provide an early indication and location of an impending fault or crack; and, to monitor the growth of the fault or crack.

For ease of description from hereinafter, including the claims, the term "structure" is used as a reference to a structure or component.

According to the present invention there is provided a system for use in the continuous monitoring of the structural integrity of a structure, said system including at least:

an elastomeric sensor pad having a first structure engaging surface and an opposite surface, said first structure engaging surface provided with a set of at least one first channels which, when said first structure engaging surface is sealingly engaged with said structure, form a corresponding set of at least one first cavities;

first fluid communication means for providing fluid communication between said set of at least one first channels and a constant vacuum source; and isolation means for isolating each of said first cavities from fluid communication with said constant vacuum source.

Preferably said system further includes means for monitoring for a variation in the vacuum condition between the constant vacuum source and said first cavities.

In one embodiment, said sensor pad further includes:

a set of at least one second channels formed on said first structure engaging surface which, when said first surface is sealingly engaged with said structure, form a corresponding set of at least one second cavities;

said second channels intersperse with said first channels; and, a second fluid communication means for providing fluid communication between said second cavities and an atmosphere or environment at a pressure different to said constant vacuum source.

Preferably said first communication means includes a third channel provided in said first surface, said third channel being in fluid communication with each of said first channels and with said constant vacuum source.

In an alternate embodiment said first fluid communication means includes a plurality of conduits, one of each providing fluid communication between respective first channels and the constant vacuum source.

Preferably said second communication means includes a fourth channel provided in the first surface, said fourth channel being in fluid communication with each of said second channels and said atmosphere or environment.

Preferably a said sensor pad is transparent or at least translucent.

Preferably the system further includes a supply of a dye indicating liquid in fluid communication with said second channels to provide a visual indication of the location of a flaw.

In an alternate embodiment said second fluid communication means comprises an opening in each of said first channels that provides fluid communication through the pad to said atmosphere environment.

Preferably said isolation means includes means for applying force to said pad at respective locations above each or selected ones of said first and/or second channels, to seal said first and/or second channels against the structure and fluidly isolate said first and/or second cavities from said vacuum source.

Preferably said isolating means is adapted to individually and/or sequentially isolate said cavities so that progressively all of said cavities are isolated from said vacuum source.

Preferably said isolating means is programmable so that the sequence of isolating said cavities can be varied.

In one embodiment, said means for applying force includes a plurality of actuators supported on or in said pad above each of said channels for applying force to sealingly deform said channel against the structure.

Preferably said actuators are electrically, magnetically, hydraulically, pneumatically, or mechanically operated.

Preferably said first communication means includes a duct formed on a second surface of said pad opposite said first surface and respective holes formed in said pad providing fluid communication between said first channels and said duct, and said isolation means includes means for applying a fluid isolation force at respective locations to obstruct said duct, to fluidly isolate selected ones of said first channels from said vacuum source.

Preferably said isolating means is adapted to individually and or sequentially isolate said cavities so that progressively all of said cavities are isolated from said vacuum source.

Preferably said isolating means is programmable so that the sequence of isolating said cavities can be varied.

In one embodiment, said means for applying force includes a plurality of actuators supported on or in said pad above each of said lengths for applying force to said pad to sealingly deform said corresponding channel against the structure.

Preferably said actuators are electrically, magnetically, hydraulically, pneumatically, or mechanically operated.

In a further embodiment, said means for applying a fluid isolation force includes a pair of minuscule pinch rollers disposed on opposite sides of said duct for sealing a length of said duct from said vacuum source to progressively isolate said first channels in communication with said length from said vacuum source.

In another embodiment, said means for applying a fluid isolation force includes a moveable seal disposed in said duct for sealing a length of said duct from said vacuum source and means for moving said seal along said duct to progressively fluidly isolate said first channels in communication with said length of said duct from said vacuum source.

In a still further embodiment, said channels extend in a radial direction.

According to the present invention there is also provided a method for continuously monitoring the integrity of a structure, said method including at least the steps of:

providing a sensor pad having a first structure engaging surface and opposite surface, the first surface provided with a set of at least one first channels;

sealingly engaging said first surface of the sensor pad with the structure so that said channels together with the structure form a corresponding set of first cavities;

coupling said first cavities to a constant vacuum source;

monitoring for a change in vacuum condition between said cavities and said constant vacuum source; and isolating each of said first cavities from said constant vacuum source.

In one embodiment, the step of isolating each of said first cavities includes venting said first cavities to the atmosphere or surrounding environment.

According to the present invention there is also provided a method for continuously monitoring the integrity of a structure, said method including at least the steps of:

providing a sensor pad having a first structure engaging surface and an opposite surface, the first surface provided with a set of at least first channels and a set of at least one second channels, said first channels isolated from and interspersed with said second channels;

sealingly engaging said first surface of the sensor pad to the structure so that said channels together with the structure form a corresponding set of first and second cavities;

coupling said first cavities to a constant vacuum source;

coupling said second cavities to an atmosphere or environment at a different pressure or vacuum condition to said constant vacuum source;

monitoring for a change the vacuum condition between said first cavities and said vacuum source; and isolating each of said first cavities from said constant vacuum source.

Preferably said step of isolating said cavities includes individually and sequentially isolating said cavities so that progressively all of said cavities are isolated from said vacuum source.

Preferably said method further includes forming said pad of a transparent or translucent material.

Preferably said method further includes the step of placing a supply of a dye indicating liquid in fluid communication with said second channels to provide a visual indication of the location of a flaw.

BRIEF DESCRIPTION OF THE DRAWINGS

Embodiments of the present invention will now be described by way of example only with reference to the accompanying drawings in which.

DETAILED DESCRIPTION OF PREFERRED EMBODIMENTS

Figure 1:
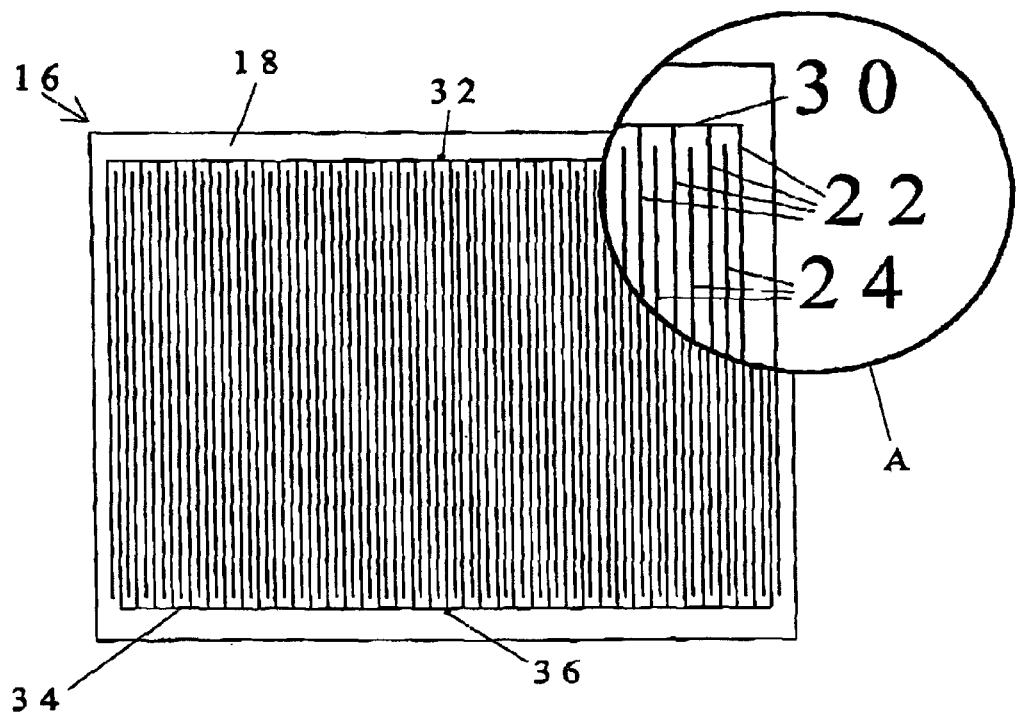
FIG. 1 is a plan view of a first structure engaging surface of a sensor pad incorporated in the a first embodiment of a system and method for the detection of a developing flaw in the structure.

As depicted in FIGS. 1–4, a system 10 (FIG. 3) for use in continuously monitoring the integrity of a structure 14 to detect the appearance of a flaw includes a sensor pad 16 having a first structure engaging surface 18 and a second opposite surface 20. The first surface 18 is provided with a set of first channels 22 and a set of second channels 24. The channels 22, 24 are represented as lines in the main portion of FIG. 1 because their widths and separation can be of the order of 250 micron. A part magnification is included as detail A in FIG. 1 to clarify this feature.

Figure 2:
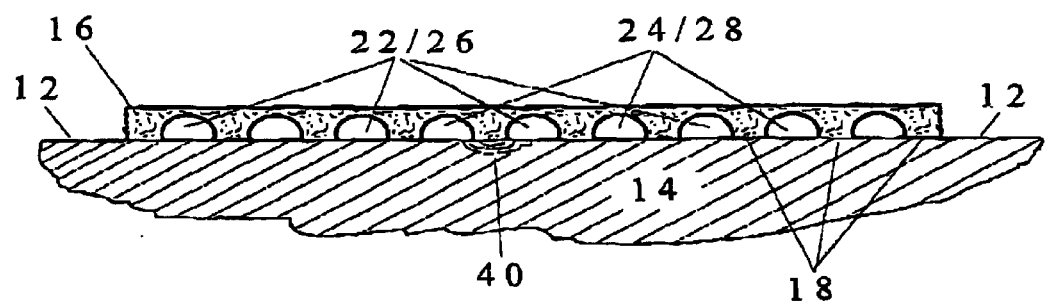
FIG. 2 shows a portion of a section though the sensor pad depicted in FIG. 1
Figure 3:
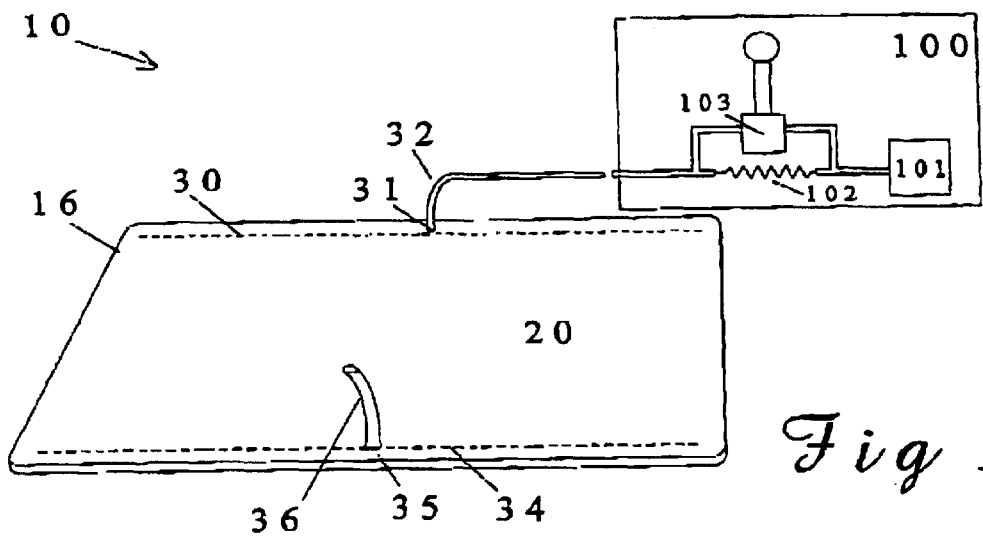
FIG. 3 shows an oblique view the sensor pad depicted in FIG. 1
Figure 4:
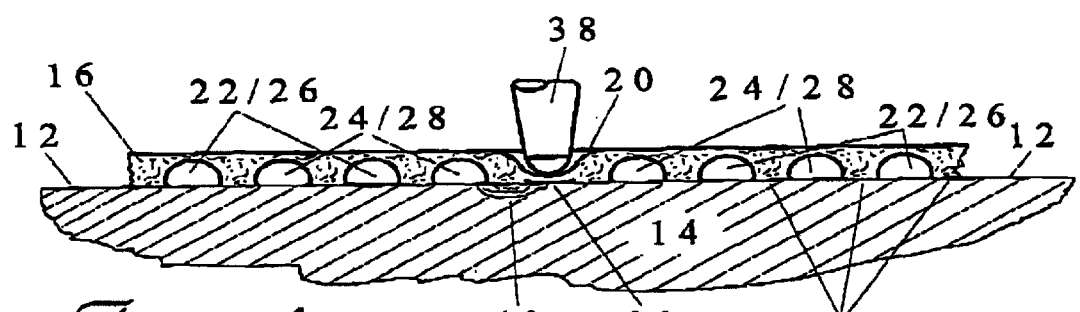
FIG. 4 shows a section though a portion of the sensor pad depicted in FIG. 1 with a channel isolating means

The first channels 22 are isolated from and interspersed with the second channels 24. As shown in FIGS. 2 and 4, when the surface 18 of the pad 16 is sealingly engaged to surface 12 of structure 14 the first channels 22 and second channels 24 together with the surface 12/structure 14 form respective sets of the first and second cavities 26 and 28. A first fluid communication means in the form of a third channel 30, through hole 31, and a conduit 32 (refer FIG. 3) provides fluid communication between the first channels 22/first cavities 26 and a constant vacuum source 101 of a monitoring apparatus 100, of the type described in the aforementioned International Application No PCT/AU94/00325 (WO 94/27130) the contents of which is incorporated herein by way of reference. (Accordingly the channels 22/cavities 26, can be termed as "vacuum" channels/cavities.) A second fluid communication means in the form of a fourth channel 34, through hole 35 and conduit 36 provides fluid communication between the second channels 24/second cavities 28 and an atmosphere environment of a different pressure or vacuum condition to the constant vacuum source. (Thus the channels 24/cavities 28 can be termed as "atmospheric" channels/cavities.)

Isolation means in the form of a plunger or probe 38 (see FIG. 4) is included in the system 10 for individually isolating the first channels 22/first cavities 26 from the vacuum source. In this embodiment the entirety of the pad 16 is made of an elastomeric material.

The probe 38 in this embodiment pushes on the surface 20 of pad 16 to sealingly deform the portion of pad 16 at location 21 over an underlying length of a channel 22/cavity 26. In this way, the channel 22/cavity 26 is isolated from communication with the channel 30 and conduit 32 and thus isolated from the vacuum source 101. As explained in greater detail below, the probe 38 can be moved or repositioned above and/or along the length of each of the channels 22/cavities 26 or common channel 30 to individually isolate or group isolate the cavities from the vacuum source.

Assume, the conduit 32 is now connected to a monitoring apparatus 100, (FIG. 3) of the type described in the aforementioned International Application No PCT/AU94/00325 (WO 94/27130).

The monitoring apparatus 100 includes the vacuum source 101 coupled in series with a high fluid flow impedance 102 and a differential pressure transducer 103 that is connected across the high impedance 102 fluid flow means so as to monitor any change in the vacuum condition between the vacuum source and the vacuum in the channels 22/cavities 26. If a crack or fault 40 (shown in FIG. 2) were to develop in the structure 14 and open onto the surface 12 and propagate so as to form a fluid communication path between one of the channels 22/cavities 26 and an adjacent channel 24/cavity 28 there will be a change in the vacuum condition of the channel 22/cavity 26 in question. This change is detected by the monitoring apparatus 100 thereby providing an indication as to the initial formation of the crack or fault 40.

However, this merely provides an indication that the crack or fault 40 exists somewhere within the area of the pad 16. To more specifically locate the position of the fault or crack 40 the isolating means, in the form of probe 38 is applied to the surface 20 sequentially at points above along common channel channel 30 to determine the affected channel 22 then sequentially along the affected channel 22. The magnitude of the force applied by the probe 38 is sufficient to sealingly flatten the channels 30 or 22 against the structure 14 to thereby seal the corresponding cavity 26. If, upon applying this force, there is no change in the reading of the monitoring apparatus then the crack or fault 40 does not underlie or is not in fluid communication with the particular channels 22/cavities 26 or channel 22/cavity 26. However, when there is a change in the vacuum condition indicated by the monitoring apparatus upon the application of the force by the probe 38 then a portion of the crack or fault 40 is disposed beneath or contained within the now isolated portion of that particular channel channels 22/cavities 26 or 22/cavity 26.

The probe 38 can be in the form as depicted in FIG. 4 so as to isolate only a single individual channel 22 at any one time. Alternately, the isolating means can be formed to sequentially isolate each of the channels 22 so as to progressively seal each and every one of the channels 22.

In the above described method, the probe 38 is applied to the vacuum channels 22/cavities 26. However it should be understood that essentially the same effect can be achieved by applying the probe to the "atmospheric" channel 24/cavities 28. Clearly, if the probe 38 is applied to a portion of the pad 16 to seal an atmospheric channel 24/cavity 28 at a location between a crack 40 and the fourth channel 34 (and assuming that the crack 40 is also in fluid communication with an adjacent "vacuum" channel 22/recess 26) then the monitoring apparatus will indicate a change in the vacuum condition because there is now no leakage to the atmosphere. By progressive isolation with a probe 38, the location of a flaw 40 can be determined.

Figure 5:
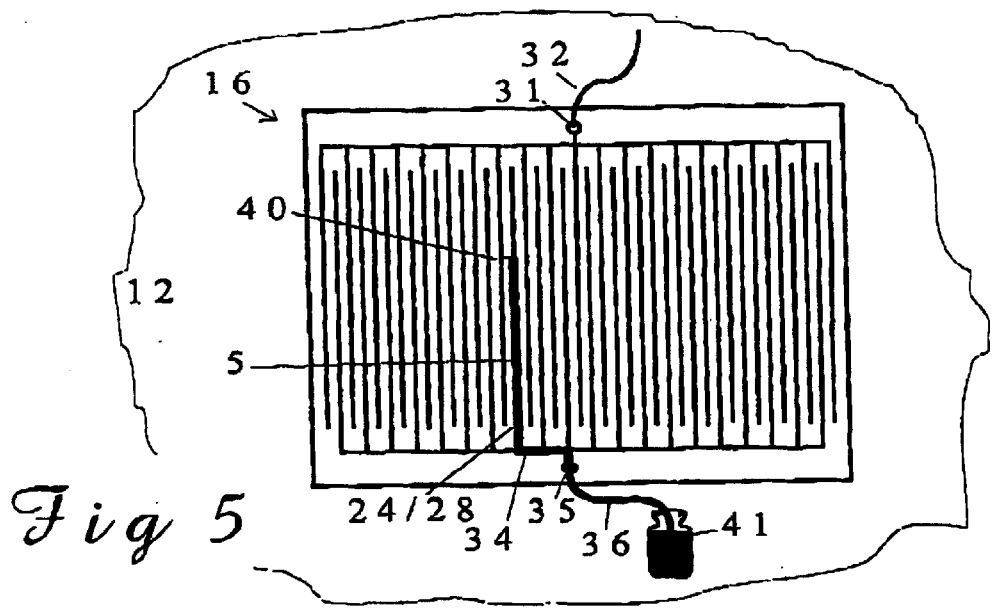
FIG. 5 shows a schematic form of the sensor pad depicted in FIG. 1 with liquid dye indicating the location of a flaw.

Instead of, or in addition to, use of a probe 38, a dye can be used to visually indicate the location of a flaw. This is illustrated in FIG. 5 which shows a plan view of a transparent sensor pad 16 made from a transparent or translucent material attached to a the surface 12. It is shown schematically, because of the problem of scale noted above. Upon detection of a flaw, a supply 41 of a liquid dye 5 is coupled in fluid communication with channels 24/cavities 28 via conduit 36, holes 35 and channel 34. The dye 5 slowly draws into the cavities 28 and substantially halts upon encountering the crack 40 because of the high fluid impedance the crack 40 presents to the dye compared to the prior passage of air. Thus providing a visual indication of the location of the crack 40.

Figure 7:
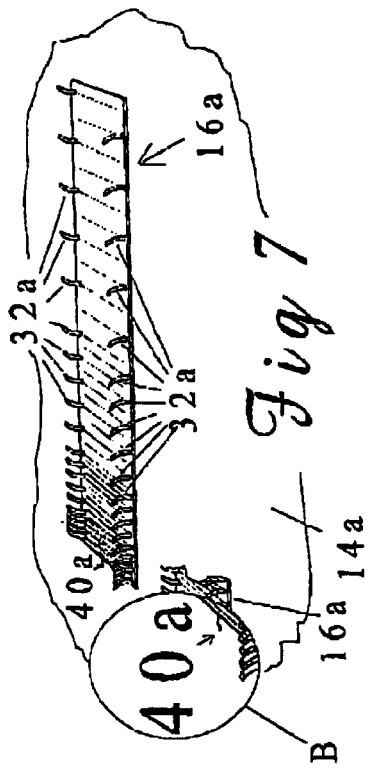
FIG. 7 is an oblique view of the sensor pad shown in FIG. 6 configured for determining crack growth rate and including a magnified insert.
Figure 6:
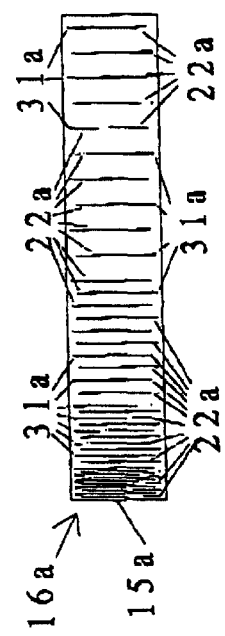
FIG. 6 is a plan view of a first structure engaging surface of a sensor pad incorporated in the system and method configured for determining crack growth rate.
Figure 8:
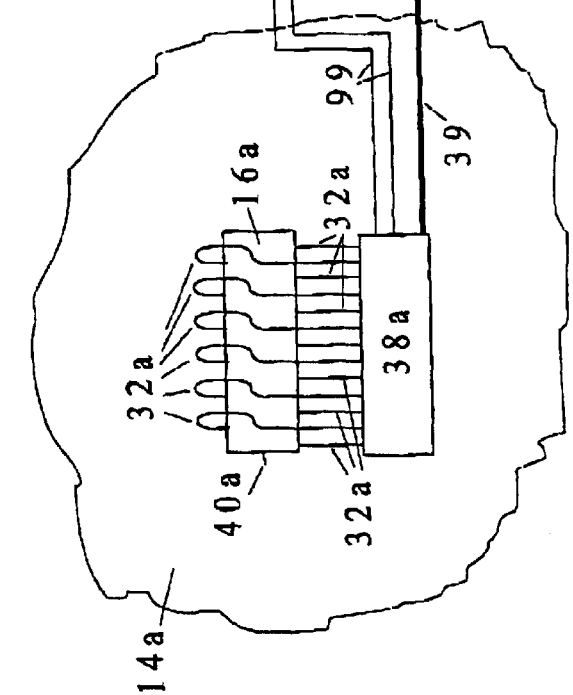
FIG. 8 is a schematic view of the sensor pad shown in FIG. 6 connected to an actuating means for sequential isolation of connections from the vacuum monitoring system.

FIGS. 6–8 illustrate how the embodiment of a system 10a can be used for tracking the propagation of a fault flaw or crack 40 in the event that a fault or crack has been detected or is known to exist. In this method, an alternative pad 16a is at a location disposed so that the crack 40 extends from the edge 15a of the pad 16a and thus is in communication with the surrounding atmosphere. The pad 16a is constructed with only the channels 22a and with individual alternate end connection via through holes 31a to respective conduits 32a as shown in FIGS. 6, 7, & 8. Further the spacing of the channels 22a progressing from the crack at edge 15a can be configured to increase. This is for convenience in measuring crack growth rate, due to the accelerating rate of propagation of fatigue cracking.

FIG. 6 is a plan view of the first structure engaging surface of the sensor pad 16a showing the channels 22a, their stepped increased spacing, and their individual connection, via through holes 31a, to the conduits 32a (FIG. 7).

FIG. 7 is an oblique view of the sensor pad 16a shown in FIG. 6 and shows the conduits 32a and a crack 40a. An additional part magnification of the region of the crack 40a is included and shown as detail B.

FIG. 8 is a schematic view of the sensor pad 16a shown in FIGS. 6 and 7 connected to an actuating isolating means 38a for sequential controllable isolation of connections channels 22a from the vacuum monitoring system 100. The isolating means 38a is in the form of a switch or multiplexer and selectively controls fluid communication between the conduits 32a (and thus channels 22a) and the system 100, or more particularly the vacuum source 101 of the system 100. The sequential isolating or means 38a may be rotary, linear, or as desired otherwise, and operates by selectively closing fluid communication between conduits 32a and the vacuum source 101. Similar fluid switching devices have been used in the past for individual connection of test points in wind tunnels to pressure transducers which where expensive in the past. However with the present device, the isolating means 38a and associated conduits 32a should be as volumetrically small as practicable to reduce time lag and hence improve sensitivity of the system 10a.

Assume that the fault or crack 40a extends to the edge 15a of the pad 16a but has not yet propagated to intersect the first of the channels 22a. In this situation, the monitoring apparatus will not detect any change in vacuum condition thus indicating that the fault or crack has not propagated to the first of the channels 22a. In time, if and when the fault or crack 40 propagates to the first of the channels 22a, the monitoring apparatus 100 will detect the change in vacuum condition. At this time, the intersected channel 22a can be isolated from the constant vacuum source by some form of isolating means, the isolator 38a closing fluid communication between the corresponding conduit 32a and the vacuum source 101. Optionally, if desired, once isolated the channel 22a can be totally de-coupled from the vacuum monitoring system and vented to the atmosphere. This isolation/venting can occur automatically upon the detection of a predetermined variation in the vacuum condition. A convenient feed back loop exists in that an electrical switching means incorporated in a monitoring circuit 104 of system 100 can be used to drive a miniature reduction drive electric motor or similar actuating means incorporated in the isolator 38a to sequentially close conduits 32a until a fall in differential pressure due to the resultant fluid isolation occurs and parks the isolating means in the new position. Alternatively, a predetermined stepper motor/microprocessor programmed arrangement may be employed Once the first of the intersected channels 22a has been isolated and/or de-coupled, the monitoring apparatus 100 returns to a steady state reading until the crack or fault 40a propagates so to intersect the next vacuum channel 22a. In this way the propagation path of the crack can be very accurately recorded. Also, by running an isolating means probe 38 as shown in FIG. 4 along the effected vacuum channel 22a upon the detection of the crack intersecting the channel 22a, the location of the intersection point of the crack 40 with the vacuum channel 22a can be pinpointed thus allowing accurate depiction of the propagation path of the crack or fault 40.

In fatigue tests to date, optical confirmation measurement has shown the method to record extremely accurate crack length markers of 0.5 mm length increments. As yet the lower limits have not been determined.

Figure 9:
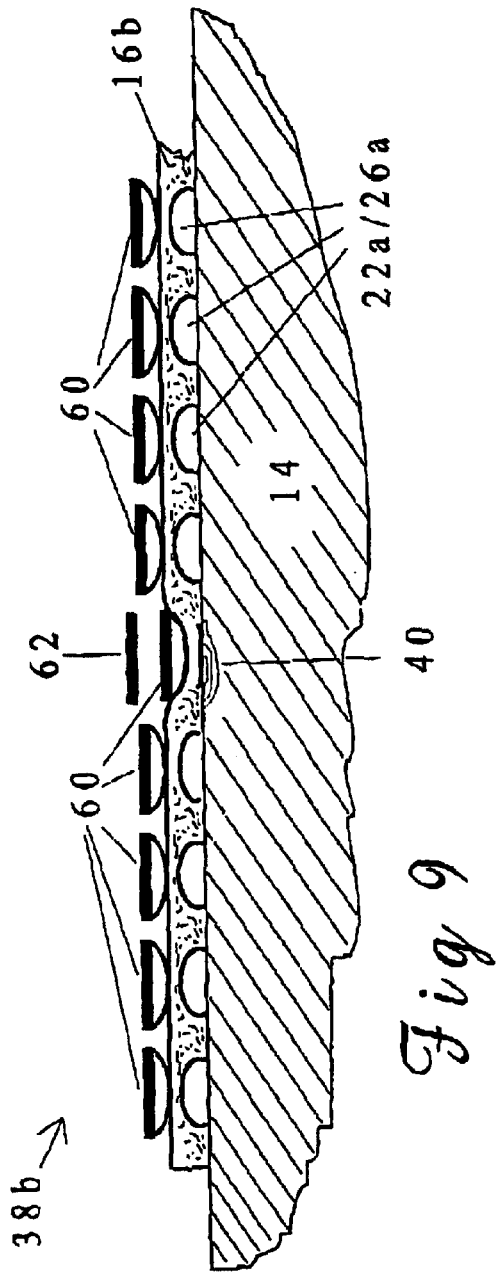
FIG. 9 is a sectional view of a pad similar to the one illustrated in FIGS. 6 & 7 showing integral isolating means comprising a plurality of actuators to sealingly deform corresponding channels against a structure, for determining crack growth rate.
Figure 10:
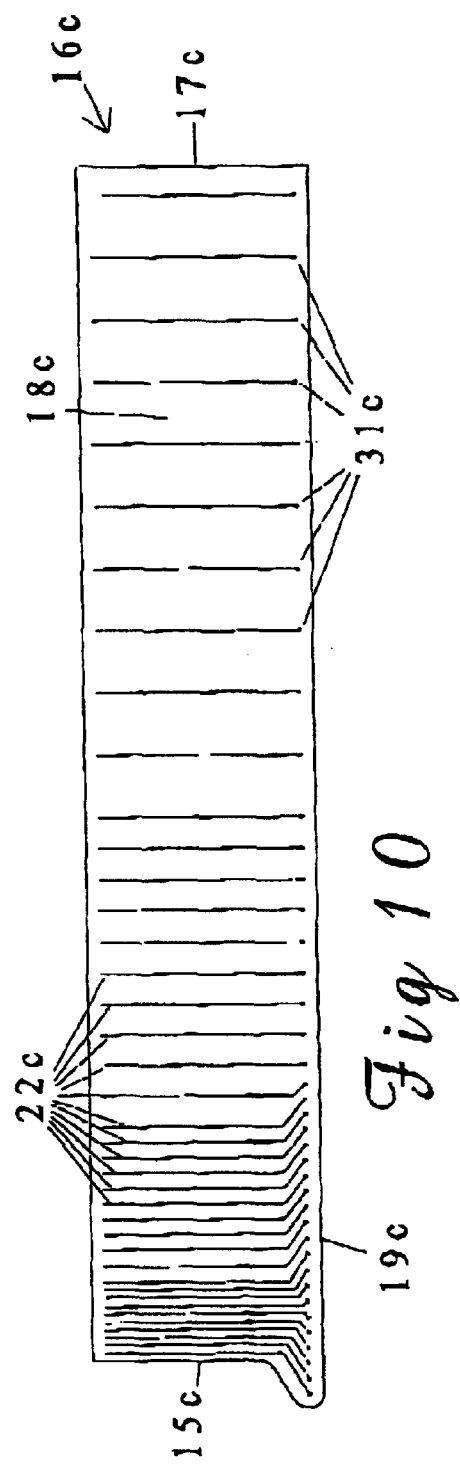
FIG. 10 is a plan view of a first structure engaging surface of a sensor pad, configured to suit an integral isolating means for determining crack growth rate.
Figure 11:
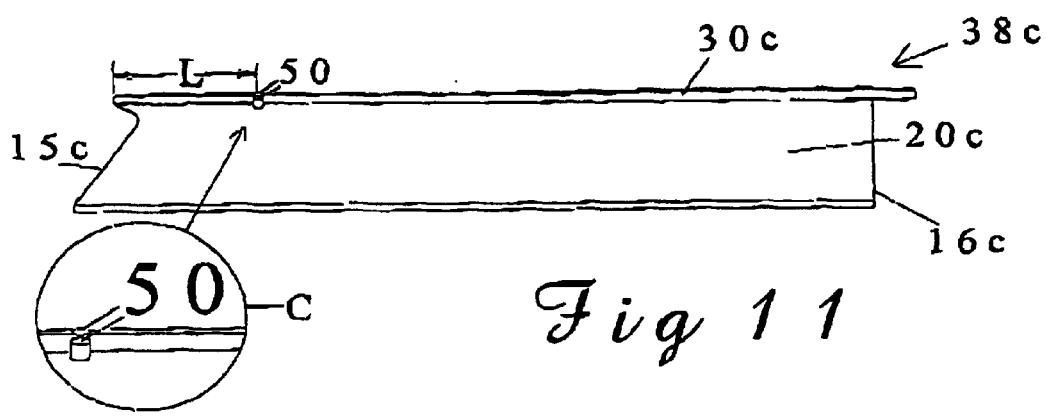
FIG. 11 is an oblique view of the sensor pad shown in FIG. 10 including parts of an integral isolating means.
Figures 12A, 12B:
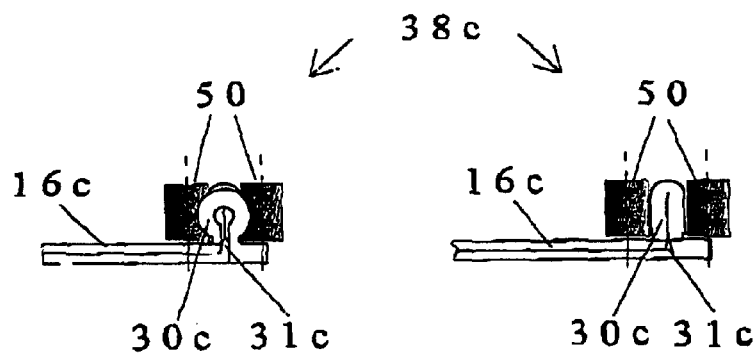
FIGS. 12a and 12b show widthwise cut section views of a portion of the sensor pad of FIG. 11 depicting progressive function of the isolating means of FIG. 11.
Figure 13:
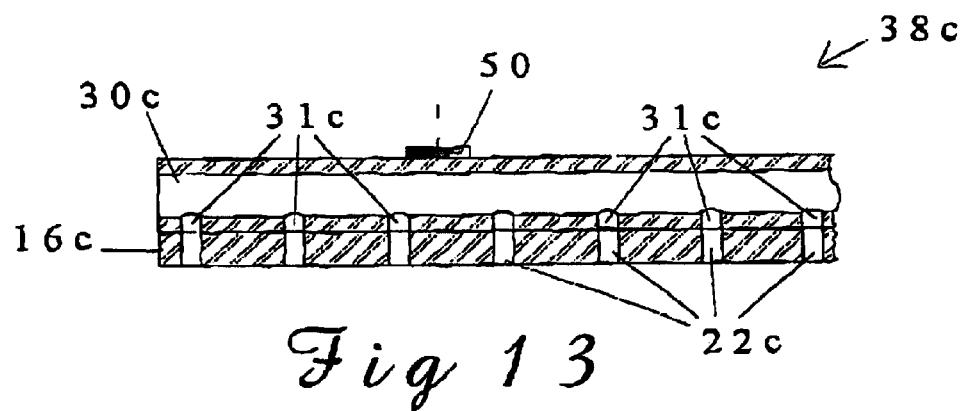
FIG. 13 is a view of a portion of the sensor pad of FIGS. 11 & 12 above showing a lengthwise cut section through the fluid isolating means of FIGS. 11, 12a & 12b.

FIG. 9 depicts a further embodiment of the system in which the isolating means 38b is magnetically operated. Here, the isolation means 38b comprises a plurality of actuators 60 which are embedded in pad 16b. The actuators 60 are in the form of magnetic plungers. The isolation means 38b also includes a dynamic magnet 62 that is mounted in a support (not shown) so as to be capable of movement along the portion above each of the actuators 60. The actuators 60 and magnet 62 are of the same magnetic pole. Accordingly, by sliding the dynamic magnet 62 over a particular actuator 60, the actuator 60 is forced in a downward direction sealingly compressing the underlying channel 22a/cavity 26. A programmable stepper motor (not shown) can be provided to control the motion and position of the dynamic magnet 62 so as to isolate the channels 22a/cavities 26 in any desired sequence.

FIGS. 10–14 depict components of a further embodiment of the system. This embodiment includes a sensor pad 16c having a plurality of first channels 22c only that are spaced apart by progressively increasing distances from edge 15c of the pad to opposite edge 17c. The end of each channels 22c adjacent longitudinal edge 19c of the pad is provided with respective through holes 31c. Through holes 31c communicate with first communication means which, in this embodiment, is in the form of a duct 30c (communal duct) formed integrally with the pad 16c and extending along the opposite or back side 20c of the pad 16c. The communal duct 30c is placed in fluid communication with a system 100 of the type depicted in FIG. 3 so as to provide fluid communication between the channels 22c and a constant vacuum source 101.

The duct 30c in this embodiment also forms part of the isolating means 38c for controllably isolating the channels 22c (and associated cavities 24c) from the vacuum source. The isolating means 38c includes a pair of pinch rollers 50 disposed on opposite sides of the duct 30c. Counter directed torque is applied to the rollers 50 to cause them to travel along the duct 30c pinching the duct 30c shut therebetween. As this occurs, a length L1 of the duct 30c behind the rollers 50 is effectively isolated from the vacuum source 101. Accordingly the channels 22c which are in communication with the length L1 via respective holes 31c are also isolated from the vacuum source 101. In this way, the isolating means 38c can progressively isolate all of the channels 22c from the vacuum source.

Figure 14:
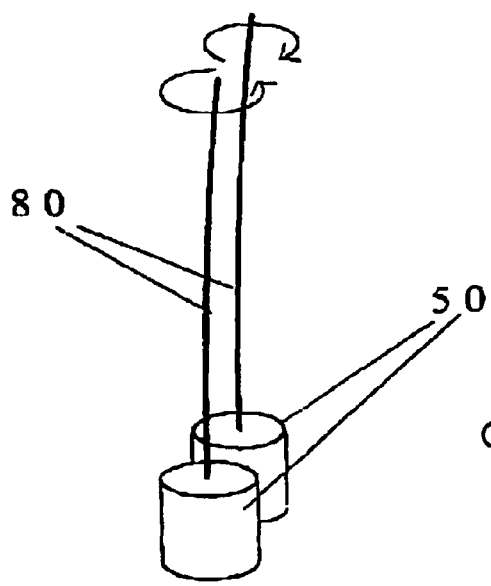
FIGS. 14 & 15 show mechanical drive configurations for the isolating means shown in FIGS. 11, 12 & 13.

FIG. 14 depicts one method and structure of imparting torque to the rollers 50. In this embodiment, each of the rollers 50 is attached to a flexible wire drive shaft 80 which are driven by either a single motor and gearbox or by two separate motors (not shown).

Figure 15:
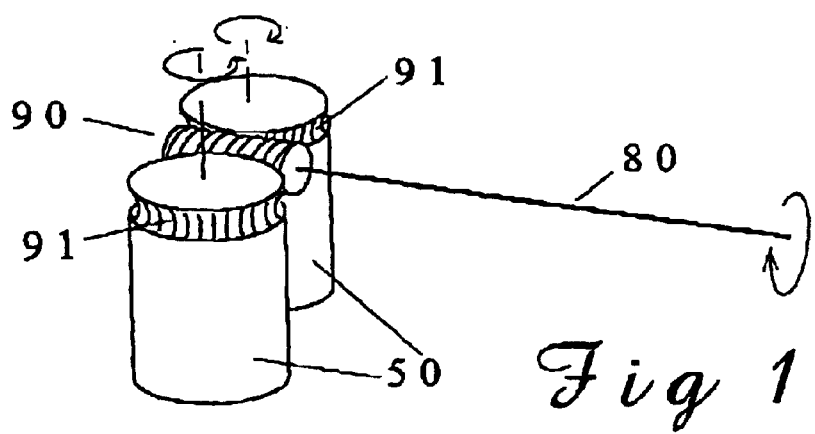

FIG. 15 depicts an alternate drive arrangement for the rollers 50. In this embodiment, a worm screw 90 meshes with respective ring gears 91 formed at adjacent axial ends of the rollers 50, the worm screw 90 being coupled to a flexible drive shaft 80 which in turn is driven by a motor (not shown).

Figure 16:
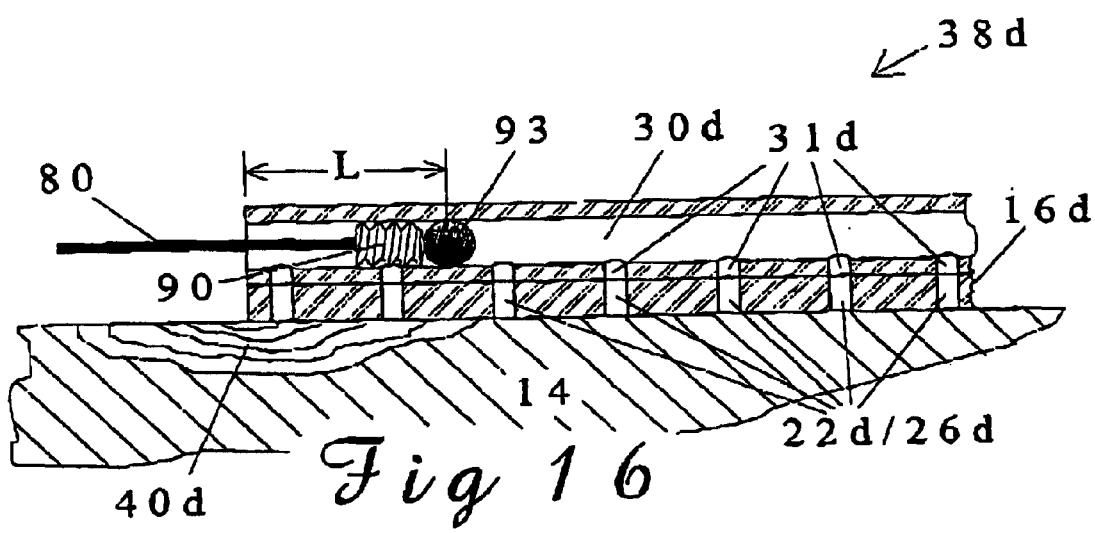
FIG. 16 is a similar view to FIG. 13 showing an alternative isolating means.

FIG. 16 depicts a further embodiment of the isolating means 38d. In this embodiment, the isolating means 38d includes a spherical seal 93 and means in the form of a worm screw 90 for moving the seal 93 along the duct 30d. The seal 93 seals a length L1 of the duct 30d from the vacuum source of the system 100. In this regard the system 100 communicates with an end of the duct 30d on a side of the seal 93 opposite the worm screw 90. The drive is imparted to the worm screw 90 from a motor (not shown) via a flexible wire drive shaft 80. It will be appreciated that the seal 93 effectively seals the channels 22d and associated cavities 26d which communicate with length L1 from the vacuum source. The worm screw 90 self taps its way along the inside of duct 30d. While the seal 93 is depicted as a spherical seal in this embodiment, other shapes are possible such as a cylindrical slug or billet with a rounded forward end. It is envisaged that the embodiment 38d with the worm screw 90 and seal 93 in those circumstances may be a best option from an engineering point of view as the bore of the duct 30d is typically only a nominal 0.5 mm.

In each of the examples driven by flexible wire shafting, a miniature reduction drive electric motor, stepper motor/ programmed microprocessor arrangement, or similar actuating means, controlled by the alarm circuit of the monitoring system 100 form the remaining part of the isolating means 38c and 38d.

Figure 17:
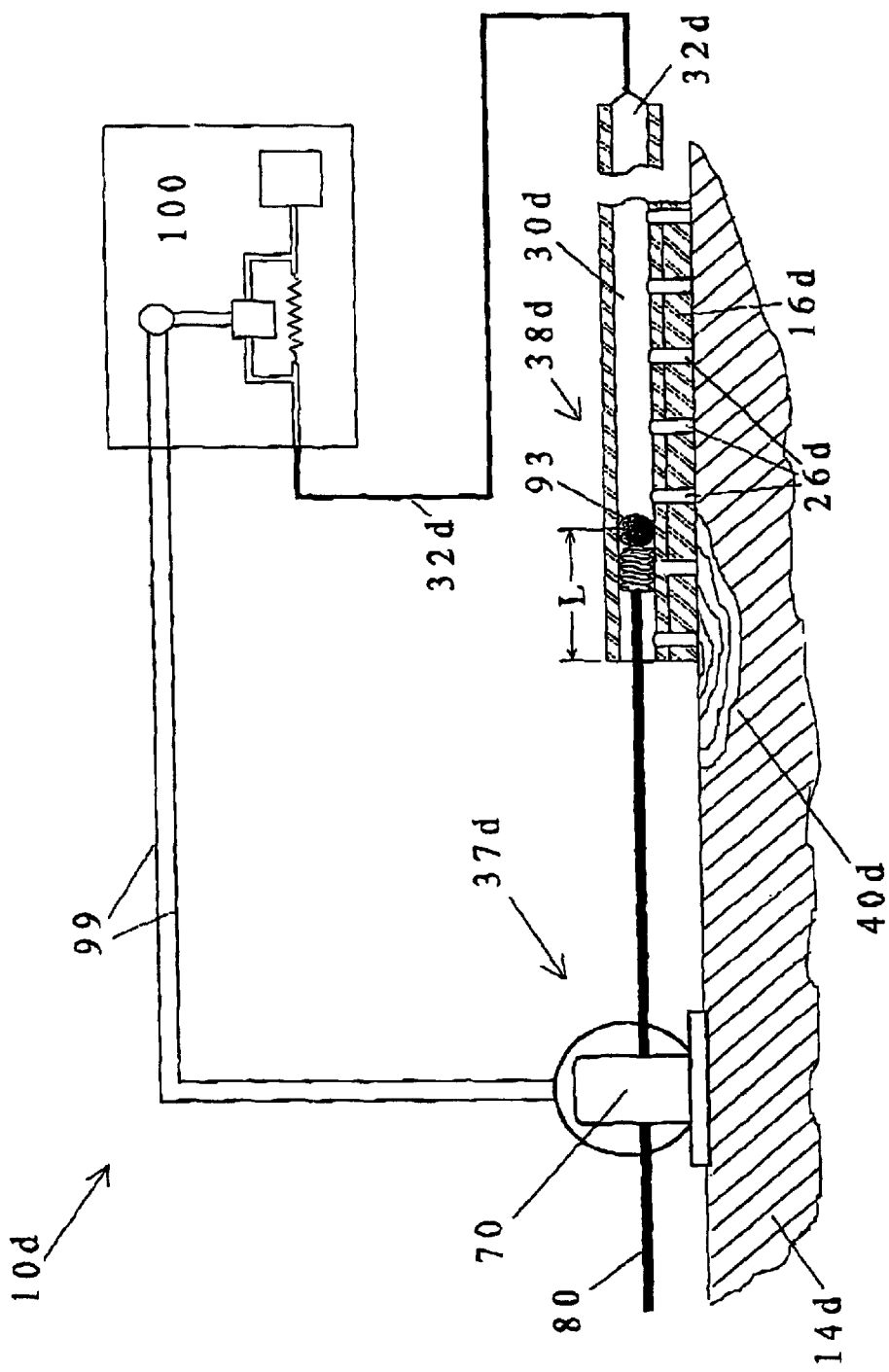
FIG. 17 shows a complete system based on the embodiment of FIG. 16.

FIG. 17 shows an example of a complete system 10d using the isolating means 38d of FIG. 16 and an actuating means 37d including; reduction drive electric motor 70 to drive shaft 80 which is longitudinally splined to allow free length-ways movement. Electrical power is supplied to the motor 70 via conductors 99, and an electrical source of the vacuum monitoring system 100, in response to adverse vacuum sensed via conduit 32d.

A crack 40d in substrate 14d is shown advancing under the pad 16d. As it progressively intercepts each cavity 26d, a rise in differential pressure, to a predetermined value, is sensed by monitor 100 via conduit 32d. In response, an electric current is communicated via conductors 99 to reduction drive electric motor 70. The motor drives the shaft 80/ propelling the screw 90/ and seal 93 through the communal duct 30d to a next isolating position resulting in a fall in differential pressure, below the predetermined value, and is sensed by the vacuum monitoring system 100 resulting in termination of electrical current to the motor 70. In this manner, accurate crack growth markers can be combined with fatigue hrs or cycles to predict propagation rates.

Figure 18:
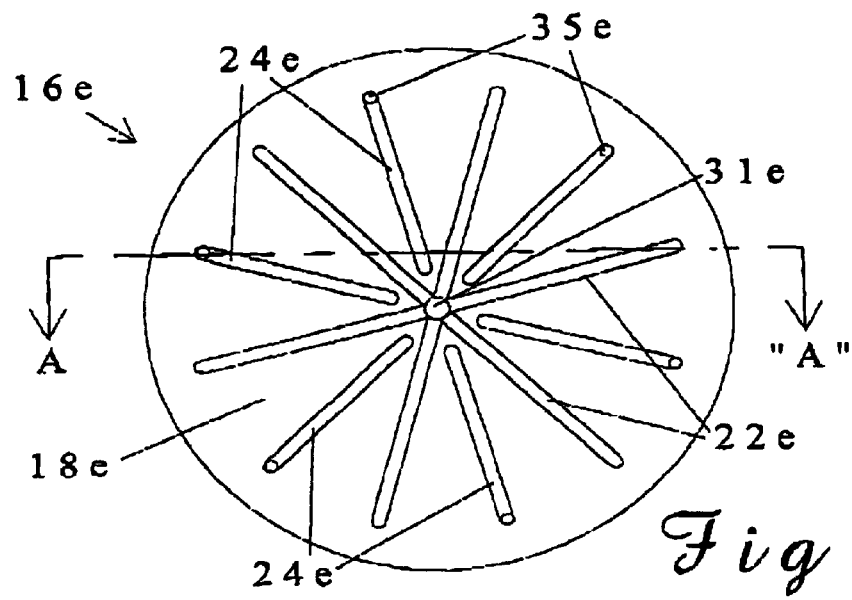
FIG. 18 shows a plan view of a first structure engaging surface of a sensor pad for placement over a rivet fastener head to determine the strain field around the fastener.
Figure 19:
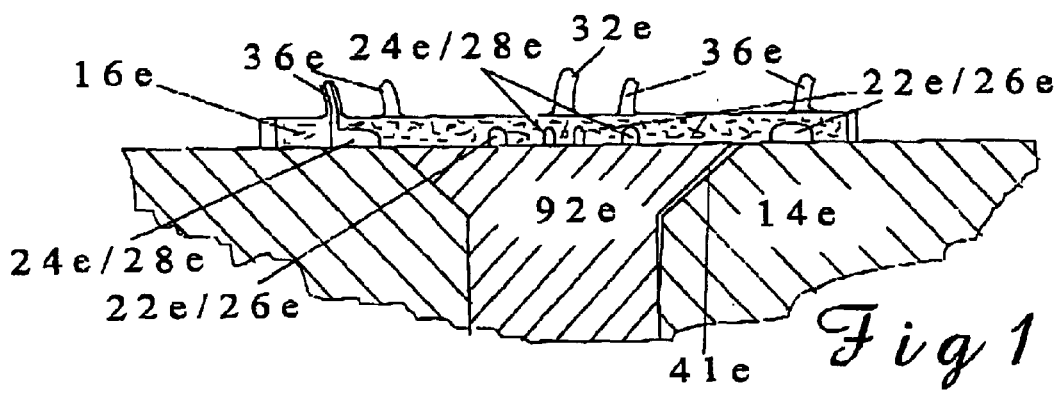
FIG. 19 shows a sectional view of the sensor pad of FIG. 18 applied over a rivet fastener head.
Figure 20:
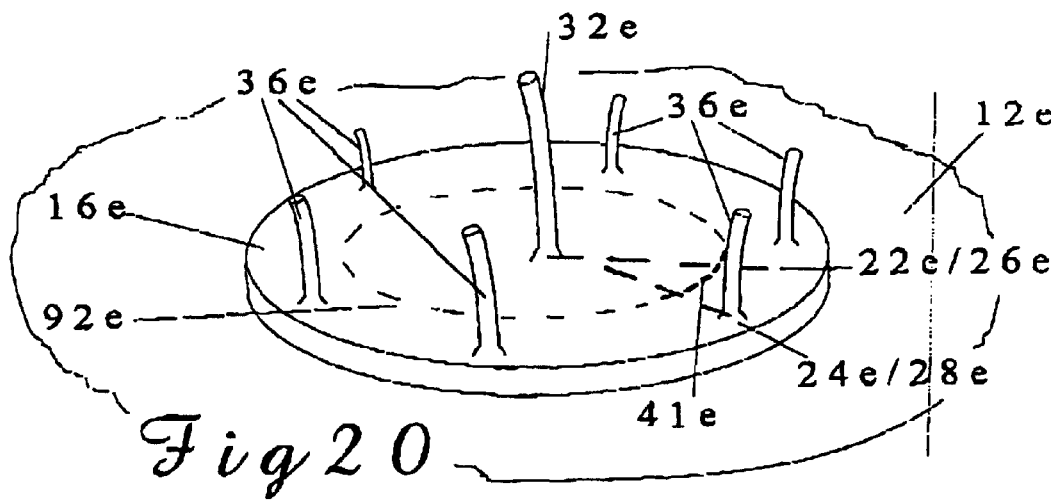
FIG. 20 shows an oblique view of the sensor pad of FIGS. 18 & 19

FIGS. 18, 19 and 20 relate to a flaw produced by plastic yield rather than an actual crack FIG. 18 shows a plan view of a first structure engaging surface 18e of a sensor pad 16e for placement over a rivet fastener head to determine the strain field around the fastener. It has a radial configuration of vacuum channels 22b with a common connection to a conduit 32e via a through hole 31e. Further, it has interspersed atmospheric channels 24e communicated at their outer ends via through holes 35e to atmospheric conduits 36e.

FIG. 19 shows a view of the sensor pad 16e of FIG. 18 sectioned through the line A—"A" and placed over a similar section through a rivet fastener head 92e and fastened component 14e.

FIG. 20 shows an oblique view of the sensor pad 16e placed on the surface 12e of the component 14e. The circumference of the underlying head of rivet 92e is shown lightly in phantom. The conduit 32e is connected to the vacuum monitoring system 100, not shown. A segment of the circumference in heavy phantom, 41e, is a separation of the interface between the rivet 92e and the adjacent portion of the hole in component 14e (see also FIG. 19. This is as a result of elastic or plastic flow in the material of the fastening. Leakage flow between the vacuum cavity 22e/26e and atmospheric cavity 24e/28e is detected and measured by the vacuum monitoring system 100. By selectively isolating ducts 36e the separation 41e of the interface in the fastening can be determined. Thus the system gives the first indication of yield. This is normally a difficult task especially if pre-stressing of the fastening has been carried out.

Now that embodiments of the device and method for monitoring the condition of a surface have been described in detail it will be apparent to those skilled in the relevant arts that numerous modifications and variations may be made without departing from the basic inventive concepts. The pad can be made of any shape to accommodate or suit the application at hand. Also, the channels 22, 22a, 22b, 22c, 22d, & 22e, 24, 24e, 30, 30c, 30d and 34 are depicted as being on the surface 18 only of the pad 16, 16a, 16b, 16c, 16c, 16c, 16d, & 16ea. However similar channels can also be formed on the opposite surface 20 of the pad so that the said pads can simultaneously monitor the condition of the surface of adjacent adjoining structures. In this regard, the said pads can be formed as part of a bond between the structures and more particularly can be made from an elastomeric adhesive or sealant material.

Embodiments are described in which the channels 22 & 22a/cavities 26 are sealed by the application of a force either directly on the channels 22 & 22a/cavities 26, (eg. FIGS. 4 & 9) or on conduits 32c (see FIGS. 7 & 20) in fluid communication with said channels and cavities. However in an alternate embodiment, the pad 16 & 16a can be provided with conduits of the type depicted in FIGS. 7 & 8 which, instead of being acted upon externally by a compressive force, can each be provided with an internal separately actuatable valve for opening or closing the fluid communication path with the vacuum source. It is envisaged that other embodiments can be constructed in which each of the channels 22& 22a is provided with its own internal valve that can be separately controlled to open and close communication between the channel 22& 22a and the channel 30. The application of micro electronic machines will improve the practical aspects of dealing with the miniature scale of the isolating means.

All such modifications and variations together with others that would be obvious to a person of ordinary skill in the art are deemed to be within the scope of the present invention the nature of which is to be determined by the above description and appended claims.

What is claimed is:

1. A system for use in the continuous monitoring of the structural integrity of a structure, said system including at least:
   an elastomeric sensor pad having a first structure engaging surface and an opposite surface, said first structure engaging surface provided with a set of at least one first channels which, when said first structure engaging surface is sealingly engaged with said structure, form a corresponding set of at least one first cavities;
   a first fluid communication arrangement for providing fluid communication between said set of at least one first channels and a constant vacuum source; and
   an isolation mechanism for isolating each of said first cavities from fluid communication with said constant vacuum source.

2. A system according to claim 1 further including a monitoring device for monitoring for a variation in the vacuum condition between the constant vacuum source and said first cavities.

3. A system according to claim 1 wherein said sensor pad further includes:
   a set of at least one second channels formed on said first structure engaging surface which, when said first surface is sealingly engaged with said structure, form a corresponding set of at least one second cavities;
   said second channels intersperse with said first channels; and,
   a second fluid communication arrangement for providing fluid communication between said second cavities and an atmosphere or environment at a pressure different to said constant vacuum source.

4. A system according to claim 1 wherein said first communication arrangement includes a third channel provided in said first surface, said third channel being in fluid communication with each of said first channels and with said constant vacuum source.

5. A system according to claim 1 wherein said first fluid communication arrangement includes a plurality of conduits, one of each providing fluid communication between respective first channels and the constant vacuum source.

6. A system according to claim 4 wherein said second communication arrangement includes a fourth channel provided in the first surface, said fourth channel being in fluid communication with each of said second channels and said atmosphere or environment.

7. A system according to claim 3 wherein said second fluid communication arrangement comprises an opening in each of said second channels that provides fluid communication through the pad to said atmosphere environment.

8. A system according to claim 3 wherein said sensor pad is transparent or at least translucent.

9. A system according to claim 7 further including a supply of a dye indicating liquid in fluid communication with said second channels to provide a visual indication of the location of a flaw.

10. A system according to claim 3 wherein said isolation mechanism includes a mechanism for applying force to said pad at respective locations above each or selected ones of said first and/or second channels, to seal said first and/or second channels against the structure and fluidly isolate said first and/or second cavities from said vacuum source.

11. A system according to claim 1 wherein said isolation mechanism is adapted to individually and/or sequentially isolate said cavities so that progressively all of said cavities are isolated from said vacuum source.

12. A system according to claim 1 wherein said isolation mechanism is programmable so that the sequence of isolating said cavities can be varied.

13. A system according to claim 10 wherein said mechanism for applying force includes a plurality of actuators supported on or in said pad above each of said channels for applying force to sealingly deform said channels against the structure.

14. A system according to claim 1 wherein said first communication arrangement includes a duct formed on a second surface of said pad opposite said first surface and respective holes formed in said pad providing fluid communication between said first channels and said duct, and said isolation mechanism includes a mechanism for applying a fluid isolation force at respective locations to obstruct said duct, to fluidly isolate selected ones of said first channels from said vacuum source.

15. A system according to claim 14 wherein said mechanism for applying a fluid isolation force includes a pair of minuscule pinch rollers disposed on opposite sides of said duct for sealing a length of said duct from said vacuum source to progressively isolate said first channels in communication with said length from said vacuum source.

16. A system according to claim 14 wherein said mechanism for applying a fluid isolation force includes a moveable seal disposed in said duct for sealing a length of said duct from said vacuum source and a system for moving said seal along said duct to progressively fluidly isolate said first channels in communication with said length of said duct from said vacuum source.

17. A method for continuously monitoring the integrity of a structure, said method including at least the steps of:
   providing a sensor pad having a first structure engaging surface and opposite surface, the first surface provided with a set of at least one first channels;
   sealingly engaging said first surface of the sensor pad with the structure so that said channels together with the structure form a corresponding set of first cavities;
   coupling said first cavities to a constant vacuum source;
   monitoring for a change in vacuum condition between said cavities and said constant vacuum source; and
   isolating each of said first cavities from said constant vacuum source.

18. A method according to claim 17 wherein the step of isolating each of said first cavities includes venting said first cavities to the atmosphere or surrounding environment.

19. A method for continuously monitoring the integrity of a structure, said method including at least the steps of:
   providing a sensor pad having a first structure engaging surface and an opposite surface, the first surface provided with a set of at least first channels and a set of at least one second channels, said first channels isolated from and interspersed with said second channels;
   sealingly engaging said first surface of the sensor pad to the structure so that said channels together with the structure form a corresponding set of first and second cavities;
   coupling said first cavities to a constant vacuum source;
   coupling said second cavities to an atmosphere or environment at a different pressure or vacuum condition to said constant vacuum source;
   monitoring for a change the vacuum condition between said first cavities and said vacuum source; and
   isolating each of said first cavities from said constant vacuum source.

20. A method according to claim 19 wherein said step of isolating said cavities includes individually and sequentially isolating said cavities so that progressively all of said cavities are isolated from said vacuum source.

21. A method according to claim 19 further including forming said pad of a transparent or translucent material.

22. A method according to claim 21 further including the step of placing a supply of a dye indicating liquid in fluid communication with said second channels to provide a visual indication of the location of a flaw.

23. A system for use in the continuous monitoring of the structural integrity of a structure, said system including at least:

an elastomeric sensor pad having a first structure engaging surface and an opposite surface, said first structure engaging surface provided with a set of at least one first channels and a set of at least one second channels interspersed with said first channels which, when said first structure engaging surface is sealingly engaged with said structure, form respective corresponding sets of at least one first cavities and at least one second cavities;

a first fluid communication arrangement for providing fluid communication between said set of at least one first channels and a constant vacuum source;

a second fluid communication arrangement for providing fluid communication between said second cavities and an atmosphere or environment at a pressure different to said constant vacuum source; and, an isolation mechanism for isolating each or selected ones of said first and/or second channels, to seal said first and/or second channels against the structure and fluidly isolate said first and/or second cavities from said vacuum source.

24. A system for use in the continuous monitoring of the structural integrity of a structure, said system including at least:

an elastomeric sensor pad having a first structure engaging surface and an opposite surface, said first structure engaging surface provided with a set of at least one first channels which, when said first structure engaging surface is sealingly engaged with said structure, form a corresponding set of at least one first cavities;

a first fluid communication arrangement for providing fluid communication between said set of at least one first channels and a constant vacuum source; and an isolation mechanism for individually and/or sequentially isolating said cavities so that progressively all of said cavities are isolated from said vacuum source.

25. A system for use in the continuous monitoring of the structural integrity of a structure, said system including at least:

an elastomeric sensor pad having a first structure engaging surface and an opposite surface, said first structure engaging surface provided with a set of at least one first channels which, when said first structure engaging surface is sealingly engaged with said structure, form a corresponding set of at least one first cavities;

a first fluid communication arrangement for providing fluid communication between said set of at least one first channels and a constant vacuum source;

an isolation mechanism for isolating each of said first cavities from fluid communication with said constant vacuum source;

wherein said first communication arrangement includes a duct formed on a second surface of said pad opposite said first surface and respective holes formed in said pad providing fluid communication between said first channels and said duct, and said isolation mechanism includes a mechanism for applying a fluid isolation force at respective locations to obstruct said duct, to fluidly isolate selected ones of said first channels from said vacuum source.

26. A system according to claim 25 wherein said mechanism for applying a fluid isolation force includes a pair of minuscule pinch rollers disposed on opposite sides of said duct for sealing a length of said duct from said vacuum source to progressively isolate said first channels in communication with said length from said vacuum source.

27. A system according to claim 25 wherein said mechanism for applying a fluid isolation force includes a moveable seal disposed in said duct for sealing a length of said duct from said vacuum source and a system for moving said seal along said duct to progressively fluidly isolate said first channels in communication with said length of said duct from said vacuum source.

28. A method for continuously monitoring the integrity of a structure, said method including at least the steps of:

providing a sensor pad having a first structure engaging surface and an opposite surface, the first surface provided with a set of at least first channels and a set of at least one second channels, said first channels isolated from and interspersed with said second channels;

sealingly engaging said first surface of the sensor pad to the structure so that said channels together with the structure form a corresponding set of first and second cavities;

coupling said first cavities to a constant vacuum source;

coupling said second cavities to an atmosphere or environment at a different pressure or vacuum condition to said constant vacuum source;

monitoring for a change the vacuum condition between said first cavities and said vacuum source; and isolating each of said first cavities individually and sequentially from said constant vacuum source so that progressively all of said cavities are isolated from said vacuum source.

29. A method according to claim 28 further including forming said pad of a transparent or translucent material.

30. A method according to claim 29 further including the step of placing a supply of a dye indicating liquid in fluid communication with said second channels to provide a visual indication of the location of a flaw.

* * * * *